United States Patent
Nishioka et al.

(10) Patent No.: US 6,706,705 B1
(45) Date of Patent: Mar. 16, 2004

(54) QUINAZOLINE DERIVATIVES

(75) Inventors: Koichiro Nishioka, Saitama (JP); Toshihiro Takahashi, Saitama (JP); Yutaka Nomura, Chiba (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 08/809,770
(22) PCT Filed: Sep. 29, 1995
(86) PCT No.: PCT/JP95/01999

§ 371 (c)(1), (2), (4) Date: Mar. 28, 1997

(87) PCT Pub. No.: WO96/16946

PCT Pub. Date: Jun. 6, 1996

(30) Foreign Application Priority Data

Nov. 25, 1994 (JP) ................................. 6-315901

(51) Int. Cl.[7] ...................... C07D 239/95; A61K 31/505
(52) U.S. Cl. ...................... 514/218; 514/254; 544/291; 540/575
(58) Field of Search ................................. 514/218, 254; 544/291; 540/375

(56) References Cited

U.S. PATENT DOCUMENTS

| | | | | |
|---|---|---|---|---|
| 4,792,913 A | * | 12/1988 | Buckland et al. ............... | 708/3 |
| 4,816,455 A | * | 3/1989 | Shickaneder et al. ....... | 514/254 |
| 5,064,833 A | * | 11/1991 | Ife et al. .................... | 514/260 |
| 5,439,895 A | * | 8/1995 | Lee et al. .................... | 514/63 |
| 5,444,062 A | * | 8/1995 | Coe et al. .................... | 514/260 |
| 5,481,484 A | * | 1/1996 | Ogawa, deceased et al. . | 703/14 |
| 6,266,630 B1 | * | 7/2001 | Garcia-Sabiro et al. ....... | 703/14 |
| 6,560,572 B1 | * | 5/2003 | Balaram et al. .............. | 703/22 |

OTHER PUBLICATIONS

Sankyo Co., Chemical Abstracts vol. 102, No. 102:95671, 1984.*

* cited by examiner

*Primary Examiner*—Matthew V. Grumbling
(74) *Attorney, Agent, or Firm*—McAulay Nissen Goldberg Kiel & Hand, LLP

(57) ABSTRACT

The present invention provides a new compound which shows slow and continuous blood pressure reducing action and is useful as an antihypertensive agent.

The invention resides in a quinazoline derivative of the following formula (I) and its pharmaceutically acceptable salt:

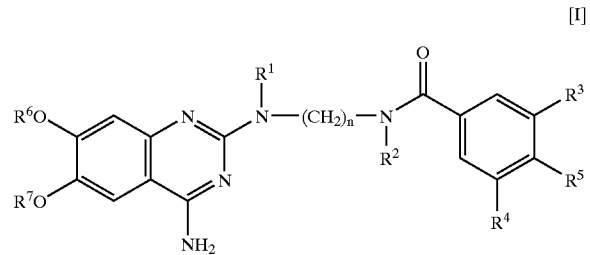

in which, each of $R^1$ and $R^2$ is H or an alkyl group of 1 to 6 carbon atoms, or $R^1$ and $R^2$ are combined to form an ethylene group; each of $R^3$ and $R^4$ is an alkyl group of 1 to 6 carbon atoms; $R^5$ is a hydrogen atom, a hydroxyl group, an alkyl group of 1 to 6 carbon atoms, or an alkoxy group of 1 to 6 carbon atoms; each of $R^6$ and $R^7$ is a hydrogen atom or an alkyl group of 1 to 6 carbon atoms; and n is 2 or 3. The invention further resides in an antihypertensive agent containing the above compound.

5 Claims, No Drawings

QUINAZOLINE DERIVATIVES

FIELD OF THE INVENTION

This invention relates to quinazoline derivatives showing slow and continuous blood pressure reducing action and an antihypertensive agent containing the same.

BACKGROUND OF THE INVENTION

An example of a quinazoline type compound employed for a known antihypertensive agent is the following compound [A] which is described in U.S. Pat. No. 3,511,836 and is commercially available as "Prazosin hydrochloride":

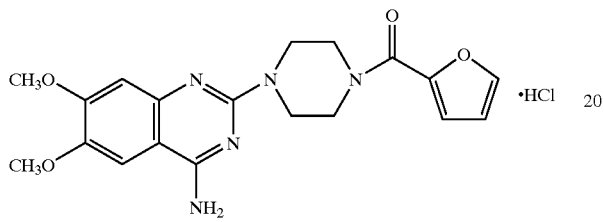

[A]

Also known is the following compound [B] of the quinazoline type antihypertensive agent which is also commercially available as "Terazosin hydrochloride":

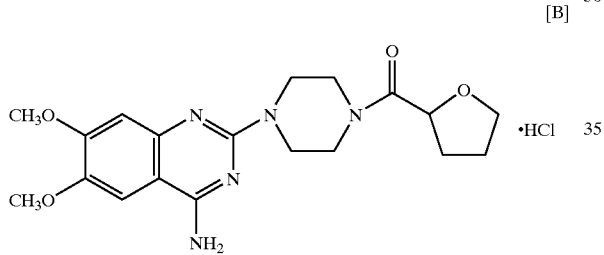

[B]

The known antihypertensive agents of the quinazoline type such as the "Prazosin hydrochloride" and "Terazosin hydrochloride" are short in their half-life in blood and show their blood pressure reducing action rapidly. Therefore, these known antihypertensive agents frequently show side-effects named "first dose phenomenon", such as orthostatic hypotension, palpitation, and tachycardia, immediately after their administration. For the reason, they have not been generally employed for treatment of hypertension at the initial stage. Recently, doxazosin mesilate which belongs to the quinazoline derivative and which shows long half-life in blood and slow blood pressure reducing action as compared with the prazosin hydrochloride has been developed. The doxazosin mesilate is reported to control blood pressure for a long time such as 24 hours by its administration once a day and seldom gives side effects such as orthostatic hypotension (J. Clin. Pharm. Ther., 14:283 (1989)).

Also known is an antihypertensive agent of a dihydropyridine type calcium antagonist. In Medical Journal (in Japanese language), vol. 30, No. 1, 101–106 (1994), this antihypertensive agent is reported to show side effects such as blush and headache after administration. These side effects arise from rapidly occurring vasolidative accessory symptoms. Therefore, the Journal indicates usefulness of Amulodipine which shows slow and continuous blood pressure reducing action. The use of the antihypertensive agent showing slow and continuous blood pressure reducing action enables administration of once a day and is effective to obviate side effects such as orthostatic hypotension and vasodilative accessory symptoms which occurs immediately after administration.

German Patent 2,457,911 describes a quinazoline derivative of the following formula [C]:

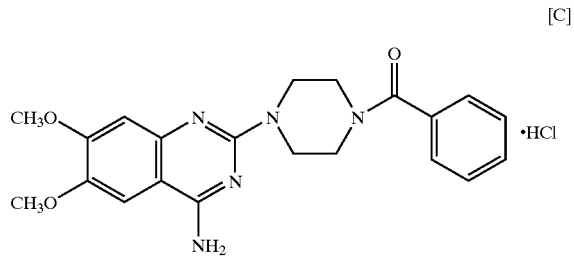

[C]

In the above patent, there is a description to the effect that the quinazoline derivative described therein shows a blood pressure reducing action, but no pharmacological data are given.

Japanese Patent Provisional Publication 59-172478 describes a quinazoline derivative of the following formula [D]:

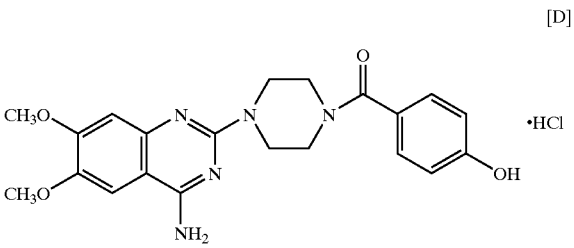

[D]

The quinazoline derivative described in the above Provisional Publication is an intermediate compound obtained in reactions and no pharmacological data are given.

Under the circumstances described above, it is considered that a new quinazoline derivative showing slow and continuous blood pressure reducing action is favorably employable as an antihypertensive agent having reduced side effects such as vasodilative accessory symptoms such as blush and headache and orthostatic hypotension.

The present invention has an object to provide a new quinazoline derivative which shows slow and continuous blood pressure reducing action.

SUMMARY OF THE INVENTION

The present invention provides a quinazoline derivative having the following formula [I] and its pharmaceutically acceptable salt:

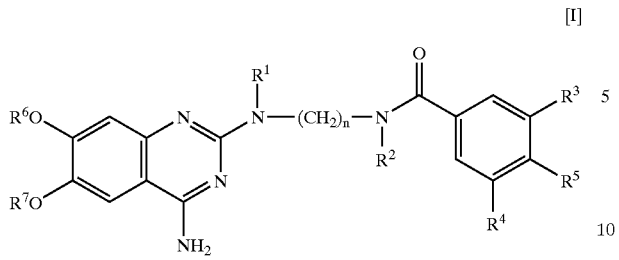

[I]

In the above formula [I], each of $R^1$ and $R^2$ independently represents a hydrogen atom or an alkyl group having 1 to 6 carbon atoms, or $R^1$ and $R^2$ are combined to form an ethylene group (—$(CH_2)_2$—); each of $R^3$ and $R^4$ independently represents an alkyl group having 1 to 6 carbon atoms; $R^5$ represents a hydrogen atom, a hydroxyl group, an alkyl group having 1 to 6 carbon atoms, or an alkoxy group having 1 to 6 carbon atoms; each of $R^6$ and $R^7$ independently represents a hydrogen atom or an alkyl group having 1 to 6 carbon atoms; and n is 2 or 3.

PREFERRED EMBODIMENTS OF THE INVENTION

The quinazoline derivative of the invention is described below in more detail.

In the aforementioned formula (I), $R^1$ and $R^2$ can be the same or different from each other and represent a hydrogen atom or an alkyl group having 1 to 6 carbon atoms such as methyl, ethyl, n-propyl, isopropyl, n-butyl, isobutyl, or t-butyl. Alternatively, $R^1$ and $R^2$ can be combined to form an ethylene group. The ethylene group is preferably formed. $R^3$ and $R^4$ represents an alkyl group having 1 to 6 carbon atoms such as methyl, ethyl, n-propyl, isopropyl, n-butyl, isobutyl, or t-butyl. $R^3$ and $R^4$ can be the same alkyl or an alkyl differing from each other. $R^5$ represents a hydrogen atom, a hydroxyl group, an alkyl group having 1 to 6 carbon atoms such as methyl, ethyl, n-propyl or isopropyl, or an alkoxy group having 1 to 6 carbon atoms such as methoxy, ethoxy, n-propoxy or isopropoxy. The hydroxyl group is preferred. $R^6$ and $R^7$ can be the same or different from each other, and represents a hydrogen atom, or an alkyl group having 1 to 6 carbon atoms such as methyl, ethyl, n-propyl, iso-propyl, n-butyl, isobutyl, or t-butyl. Methyl is preferred. n is 2 or 3, and 2 is preferred.

The pharmaceutically acceptable salt of the quinazoline derivative of the formula [I] according to the present invention can be an inorganic acid salt such as hydrochloride, sulfate, or nitrate, or an organic acid salt such as fumarate, mesylate, tosylate, oxalate, or citrate.

The quinazoline derivative of the invention can be synthesized by the following synthetic reaction process in the same manner as described in J. Med. Chem., 1986, 29, 19–25:

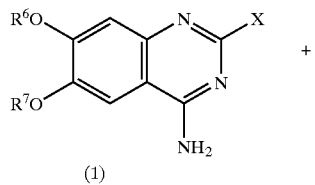

(1)

+

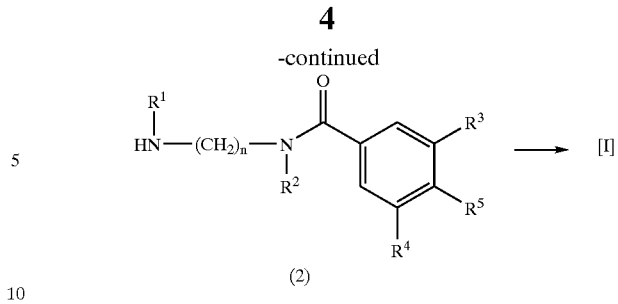

(2) → [I]

in which X represents a halogen such as chlorine or bromine, and $R^1$, $R^2$, $R^3$, $R^4$, $R^5$, $R^6$, $R^7$ and n have the same meanings as above.

The above-illustrated reaction can be performed by reacting 2-halo-4-amino-6,7-dimethoxyquinazoline (1) and the compound (2) in an inert solvent such as an aromatic hydrocarbon (e.g., benzene, toluene, or xylene), an ether (e.g., ethyl ether, tetrahydrofuran, or dioxane), an alcohol (e.g., methanol, ethanol, propanol, or butanol), an aliphatic acid ester (e.g., methyl acetate, or ethyl acetate), an aliphatic dimethyl amide (e.g., dimethyl-formamide or dimethylacetamide), or dimethyl sulfoxide. The reaction temperature is in the range of 40 to 200° C., preferably in the range of 50 to 150° C. The reaction period depends on the reaction temperature, and is in the range of 1 to 24 hours.

Alternatively, the quinazoline derivative of the formula [I] according to the invention can be synthesized in the following route:

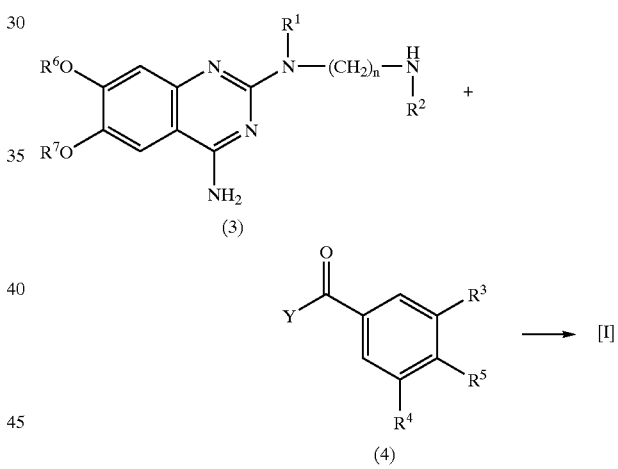

in which Y represents a halogen such as chlorine or bromine, and $R^1$, $R^2$, $R^3$, $R^4$, $R^5$, $R^6$, $R^7$ and n have the same meanings as above.

The above-illustrated reaction can be performed by reacting the compound (3) and the compound (4) in an inert solvent such as an aromatic hydrocarbon (e.g., benzene, toluene, or xylene), an ether (e.g., ethyl ether, tetrahydrofuran, or dioxane), an alcohol (e.g., methanol, ethanol, propanol, or butanol), an aliphatic acid ester (e.g., methyl acetate, or ethyl acetate), an aliphatic dimethyl amide (e.g., dimethylformamide or dimethylacetamide), or dimethyl sulfoxide. The reaction temperature is in the range of −10 to 200° C., preferably in the range of −10 to 150° C. The reaction period depends on the reaction temperature, and is in the range of 1 to 40 hours. If Y is a hydroxyl group, the reaction can be performed in the presence of a condensating agent such as 1-(3-dimethylaminopropyl)-3-ethylcarbodimide.

If each of $R^6$ and $R^7$ is a hydroxyl group, the compounds (1) and (3) can be reacted after protecting the hydroxyl groups using a protective group such as benzyl, which is removed after completion of the reaction.

Representative compounds of the aforementioned formula [I] according to the invention are described below:

(1) N-[2-[(4-amino-6,7-dimethoxy-2-quinazolinyl)-amino]ethyl]-3,5-dimethylbenzenecarboxamide
(2) N-[3-[(4-amino-6,7-dimethoxy-2-quinazolinyl)-amino]propyl]-3,5-dimethylbenzenecarboxamide
(3) N-[2-[(4-amino-6,7-dimethoxy-2-quinazolinyl)-methylamino]ethyl]-3,5-dimethylbenzenecarboxamide
(4) N-methyl-N-[3-[(4-amino-6,7-dimethoxy-2-quinazolinyl)amino]propyl]-3,5-dimethylbenzenecarboxamide
(5) N-methyl-N-[2-[(4-amino-6,7-dimethoxy-2-quinazolinyl)(methyl)amino]ethyl]-3,5-dimethyl-4-hydroxy-benzenecarboxamide
(6) N-methyl-N-[2-[(4-amino-6,7-dimethoxy-2-quinazolinyl)(methyl)amino]ethyl]-3,4,5-trimethylbenzene-carboxamide
(7) N-methyl-N-[3-[(4-amino-6,7-dimethoxy-2-quinazolinyl)(ethyl)amino]propyl]-3,5-diethyl-4-methoxy-benzenecarboxamide
(8) N-ethyl-N-[2-[(4-amino-6,7-dimethoxy-2-quinazolinyl)(ethyl)amino]ethyl]-3,5-di-n-propyl-4-hydroxybenzenecarboxamide
(9) N-[3-[(4-amino-6,7-dimethoxy-2-quinazolinyl)(n-propyl)amino]propyl]-3,5-diethylbenzenecarboxamide
(10) N-n-butyl-N-[2-[(4-amino-6,7-dimethoxy-2-quinazolinyl)(methyl)amino]ethyl]-3,5-diethyl-4-hydroxy-benzenecarboxamide
(11) N-methyl-N-[3-[(4-amino-6,7-dimethoxy-2-quinazolinyl)(t-butyl)amino]propyl]-3,5-di-t-butyl-4-hydroxybenzenecarboxamide
(12) N-isobutyl-N-[3-[(4-amino-6,7-dimethoxy-2-quinazolinyl)(ethyl)amino]propyl]-3,5-diisopropyl-4-ethoxybenzenecarboxamide
(13) N-n-propyl-N-[3-[(4-amino-6,7-dimethoxy-2-quinazolinyl)(n-propyl)amino]propyl]-3,5-dimethyl-4-hydroxybenzenecarboxamide
(14) 4-amino-2-[4-(3,5-dimethylbenzoyl)-1-piperazinyl]-6,7-dimethoxyquinazoline
(15) 4-amino-2-[4-(3,5-dimethyl-4-hydroxybenzoyl)-1-piperazinyl]-6,7-dimethoxyquinazoline
(16) 4-amino-2-[4-(3,5-diethyl-4-hydroxybenzoyl)-1-piperazinyl]-6,7-dimethoxyquinazoline
(17) 4-amino-2-[4-(3,5-diethyl-4-methoxybenzoyl)-1-piperazinyl]-6,7-dimethoxyquinazoline
(18) 4-amino-2-[4-(3,5-diisopropyl-4-methylbenzoyl)-1-piperazinyl]-6,7-dimethoxyquinazoline
(19) 4-amino-2-[4-(3,5-diisopropyl-4-hydroxybenzoyl)-1-piperazinyl]-6,7-dimethoxyquinazoline
(20) 4-amino-2-[4-(3,5-di-n-butyl-4-hydroxybenzoyl)-1-piperazinyl]-6,7-dimethoxyquinazoline
(21) 4-amino-2-[4-(3,5-di-n-butyl-4-ethoxybenzoyl)-1-piperazinyl]-6,7-dimethoxyquinazoline
(22) 4-amino-2-[4-(3,5-di-t-butylbenzoyl)-1-piperazinyl]-6,7-dimethoxyquinazoline
(23) 4-amino-2-[4-(3,5-di-t-butyl-4-hydroxybenzoyl)-1-piperazinyl]-6,7-dimethoxyquinazoline
(24) 4-amino-2-[4-(3,5-dimethyl-4-hydroxybenzoyl)-1-homopiperazinyl]-6,7-dimethoxyquinazoline
(25) 4-amino-2-[4-(3,5-dimethyl-4-methoxybenzoyl)-1-homopiperazinyl]-6,7-dimethoxyquinazoline
(26) 4-amino-2-[4-(3,5-di-n-propyl-4-hydroxybenzoyl)-1-homopiperazinyl]-6,7-dimethoxyquinazoline
(27) 4-amino-2-[4-(3,5-di-n-propyl-4-ethylbenzoyl)-1-homopiperazinyl]-6,7-dimethoxyquinazoline
(28) 4-amino-2-[4-(3,5-di-t-butylbenzoyl)-1-homopiperazinyl]-6,7-dimethoxyquinazoline
(29) 4-amino-2-[4-(3,5-di-t-butyl-4-hydroxybenzoyl)-1-homopiperazinyl]-6,7-dimethoxyquinazoline
(30) 4-amino-2-[4-(3,5-di-t-butyl-4-hydroxybenzoyl)-1-piperazinyl]-6-hydroxy-7-methoxyquinazoline
(31) 4-amino-2-[4-(3,5-di-t-butyl-4-hydroxybenzoyl)-1-piperazinyl]-7-hydroxy-6-methoxyquinazoline The quinazoline derivative of the formula [I] according to the invention can be administered through either oral or parenteral route. The oral administration is preferred. The quinazoline derivative of the invention can be formulated in the form of tablets, granules, capsules, liquid, or injections by means of conventional methods and administered in these forms. The tablets are preferred.

The dosage of the quinazoline derivative of the formula [I] according to the invention is in the range of 0.1 mg to 1 g/day for adult. The quinazoline derivative of such dosage is preferably administered once or twice a day.

Pharmacological tests for the quinazoline derivative of the formula [I] according to the invention and comparison compounds are described below.

Pharmacological Test-1

This test was performed using male spontaneously hypertensive rats (SHR, 15 weeks old or older, 300 to 400 g). Under halothane anesthesia, the left femoral arteries of the rats were cannulated using a polyethylene cannula. The cannula was connected to a device for blood pressure measurement. Then, the rats were placed in the Bollman-type cages. After one hour, it was confirmed that the blood pressure was kept constant. When the rats waked, they were orally administered with the test compound, and variation of blood pressure after the administration was measured as time passed. The test compound was suspended or dissolved in 1% aqueous methylcellulose solution and administered in an amount of 0.2 mL per 100 g of body weight. The test results are set forth in Table 1.

TABLE 1

| Compound | Dosage (mg/kg) | Number of rats | Blood Pressure (mmHg) | | | | |
|---|---|---|---|---|---|---|---|
| | | | 1 hr. | 3 hrs. | 6 hrs. | 9 hrs. | 12 hrs. |
| Con. | 0 | 2 | −2 | 6 | −4 | — | — |
| Prazo. | 1 | 2 | −35 | −41 | −42 | −41 | −38 |
| | 3 | 2 | −57 | −69 | −65 | −61 | −60 |
| Doxa. | 1 | 1 | −19 | −21 | −19 | — | — |
| | 3 | 1 | −35 | −32 | −29 | — | — |
| | 10 | 1 | −37 | −50 | −35 | — | — |
| Comp. [C] | 1 | 2 | −36 | −31 | −39 | — | — |
| | 3 | 2 | −64 | −64 | −61 | — | — |
| Comp. [D] | 1 | 2 | 2 | −3 | −6 | — | — |
| | 3 | 2 | −5 | −6 | −8 | — | — |
| Invention | 1 | 2 | −4 | −25 | −41 | −44 | −39 |
| | 3 | 2 | −29 | −60 | −75 | −64 | −60 |

Remarks:
Con.: control
Prazo.: prazosin hydrochloride
Doxa.: doxazosin mesilate
Comp. [C]: 4-amino-2-(4-benzoyl-1-piperazinyl)-6,7-dimethoxyquinazoline hydrochloride

TABLE 1-continued

| Com-pound | Dosage (mg/kg) | Number of rats | Blood Pressure (mmHg) | | | | |
|---|---|---|---|---|---|---|---|
| | | | 1 hr. | 3 hrs. | 6 hrs. | 9 hrs. | 12 hrs. |

Comp. [D]: 4-amino-2-[4-(4-hydroxybenzoyl)-1-piperazinyl]-6,7-dimethoxyquinazoline hydrochloride
Invention: 4-amino-2-[4-(3,5-di-t-butyl-4-hydroxybenzoyl)-1-piperazinyl]-6,7-dimethoxyquinazoline hydrochloride [corresponding to the aforementioned compound (23)]

As is apparent from Table 1, prazosin hydrochloride and the compound [c] give the approximately maximum blood pressure depression after a lapse of one hour, while the compound of the invention slowly decreases the blood pressure and gives the blood pressure depression at the same level after a lapse of six hours. The slow blood pressure depression by the compound of the invention is also prominent even in comparison with doxazosin mesilate. It is also apparent that the compound [D] having a chemical structure analogous to the compound of the invention gives very little blood pressure depression.

Thus, the compound of the invention shows a slow and continuous blood pressure reducing action and, therefore, is of value as an antihypertensive agent.

Pharmacological Test-2

This test was performed by measuring the blood pressure in the same manner as in the above pharmacological test-1 using male DOCA salt hypertensive rats (DOCAR, 15 weeks old or older, 300 to 400 g, not-fasted). The test results are set forth in Table 2. The compound of the invention examined in this test was the same as that employed in the pharmacological test-1.

TABLE 2

| Com-pound | Dosage (mg/kg) | Number of rats | Blood Pressure (mmHg) | | | | |
|---|---|---|---|---|---|---|---|
| | | | 1 hr. | 3 hrs. | 6 hrs. | 9 hrs. | 12 hrs. |
| Con. | 0 | 3 | −1 | +4 | −5 | 0 | +6 |
| Prazo. | 3 | 3 | −81 | −62 | −69 | −50 | −36 |
| Invention | 3 | 3 | −15 | −42 | −62 | −49 | −37 |

Pharmacological Test-3

This test was performed in the same manner as in the above pharmacological test-1 using male Dahl salt sensitive male rats (DahlSR, 15 weeks old or older, 300 to 400 g, not-fasted). The test results are set forth in Table 3. The compound of the invention examined in this test was the same as that employed in the pharmacological test-1.

TABLE 3

| Com-pound | Dosage (mg/kg) | Number of rats | Blood Pressure (mmHg) | | | | |
|---|---|---|---|---|---|---|---|
| | | | 1 hr. | 3 hrs. | 6 hrs. | 9 hrs. | 12 hrs. |
| Con. | 0 | 3 | +3 | +4 | −8 | −20 | −28 |
| Prazo. | 3 | 3 | −48 | −41 | −43 | −40 | −36 |
| Invention | 3 | 3 | −11 | −25 | −49 | −50 | −52 |

As is apparent from the results of Tables 1 and 2, prazosin hydrochloride gives the approximately maximum blood pressure depression after a lapse of one to two hours, while the compound of the invention slowly decreases the blood pressure and gives the blood pressure depression at the same level after a lapse of six hours. Thus, the compound of the invention shows a slow and continuous blood pressure reducing action and, therefore, is of value as an antihypertensive agent.

Pharmacological Test-4

This test was performed by measuring the blood pressure in the same manner as in the above pharmacological test-1 using normal male rats of Wister strain (15 weeks old or older, 300 to 400 g, not-fasted). The test results are set forth in Table 4. The compound of the invention examined in this test was the same as that employed in the pharmacological test-1.

TABLE 4

| Com-pound | Dosage (mg/kg) | Number of rats | Blood Pressure (mmHg) | | | | |
|---|---|---|---|---|---|---|---|
| | | | 1 hr. | 3 hrs. | 6 hrs. | 9 hrs. | 12 hrs. |
| Con. | 0 | 4 | 0 | −1 | −12 | −11 | −15 |
| Prazo. | 1 | 4 | −27 | −21 | −23 | −23 | −24 |
| | 3 | 2 | −44 | −40 | −33 | −33 | −43 |
| Doxa. | 3 | 3 | −24 | −19 | −20 | −22 | −23 |
| Invention | 1 | 4 | −4 | −11 | −21 | −22 | −23 |
| | 3 | 4 | −5 | −9 | −19 | −21 | −24 |

As is apparent from Table 4, prazosin hydrochloride and doxazosin mesilate both largely decrease normal blood pressure, while the compound of the invention affects the normal blood pressure only slightly. These results also suggest that the compound of the invention is of value as antihypertensive agent.

SYNTHESIS EXAMPLE

4-Amino-2-[4-(3,5-di-t-butyl-4-hydroxybenzoyl)-1-piperazinyl)-6,7-dimethoxyquinazoline hydrochloride (1) Synthesis of 1-benzyl-4-(3,5-di-t-butyl-4-hydroxybenzoyl)piperazine Under nitrogen atmosphere, 3,5-di-t-butyl-4-hydroxybenzoic acid (3.10 g, 12.4 mmol.) and 1-benzylpiperazine (2.00 g, 11.3 mmol.) were dissolved in dichloromethane. Under chilling with ice, to this solution was portionwise added 1-(3-dimethylaminopropyl)-3-ethylcarbodiimide hydrochloride (2.87 g, 15.0 mmol.), and the resulting mixture was stirred overnight at room temperature. The reaction mixture was washed successively with saturated aqueous sodium hydrogen carbonate and water, and dried over anhydrous sodium sulfate. The solvent was distilled off under reduced pressure. The residue was purified by silica gel column chromatography (chloroform/methanol=20/1), to give the desired compound as an amorphous product (5.08 g, yield: 100%).

$^1$H-NMR (CDCl$_3$)δ:

1.43 (18H, s), 2.3–2.6 (4H, m), 3.54 (2H, s), 3.5–3.7 (4H, m), 5.37 (1H, s), 7.2–7.4 (7H, m)

(2) Synthesis of 1-(3,5-di-t-butyl-4-hydroxybenzoyl)-piperazine

In tetrahydrofuan (100 mL) was dissolved the compound (5.08 g, 12.4 mmol.) obtained in (1) above. To this solution was added 10% palladium/carbon (600 mg), and the resulting mixture was stirred under hydrogen atmosphere. The reaction mixture was filtered over Celite, and the filtrate was concentrated under reduced pressure. The residue was purified by silica gel column chromatography (chloroform/methanol=30/1), to give the desired compound as a white crystalline product (1.50 g, yield: 38%).

¹H-NMR (CDCl₃)δ:
1.44 (18H, s), 2.9–3.2 (4H, m), 3.6–4.1 (4H, m)
5.45 (1H, brs), 7.23 (2H, s)

(3) Synthesis of 4-amino-2-[4-(3,5-di-t-butyl-4-hydroxy-benzoyl)-1-piperazinyl)-6,7-dimethoxyquinazoline hydro-chloride [corresponding to the aforementioned compound (23)]

In 1-butanol (30 mL) were suspended the compound obtained in (2) above (500 mg, 1.57 mmol.) and 4-amino-2-chloro-6,7-dimethoxyquinazoline (376 mg, 1.57 mmol.), and the mixture was heated under reflux for 4 hours. The reaction mixture was cooled to room temperature. The precipitated crystalline product was collected by filtration and washed with 1-butanol, to give the desired compound as a white crystalline powder product (594 mg, yield: 68%).
m.p.: 253–254° C.

¹H-NMR (DMSO-d₆)δ:
1.41 (18H, s), 3.6–3.8 (4H, m), 3.85 (3H, s),
3.89 (3H, s), 3.8–4.0 (4H, m), 7.23 (2H, s),
7.40 (1H, s), 7.43 (1H, s), 7.73 (1H, s),
8.66 (1H, brs), 8.88 (1H, brs), 12.12 (1H, s)

ABILITY FOR INDUSTRIAL USE

The quinazoline derivatives of the aforementioned formula [I] provided by the present invention are useful for treating hypertension and dysuria accompanying prostatomegaly. Further, the quinazoline derivatives of the invention show slow and continuous blood pressure reducing action with giving almost no effect to normal blood pressure, and are particularly useful as antihypertensive agents.

What is claimed is:

1. A quinazoline derivative having the following formula [I] and its pharmaceutically acceptable salt:

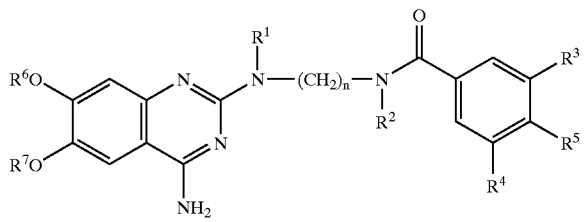

[I]

in which $R^1$ and $R^2$ are combined to form an ethylene group; each of $R^3$ and $R^4$ independently represents an alkyl group having 1 to 6 carbon atoms; $R^5$ represents a hydroxyl group; $R^6$ and $R^7$ independently represents a hydrogen atom or an alkyl group having 1 to 6 carbon atoms; and n is 2 or 3.

2. A quinazoline derivative having the following formula [I] and its pharmaceutically acceptable salt:

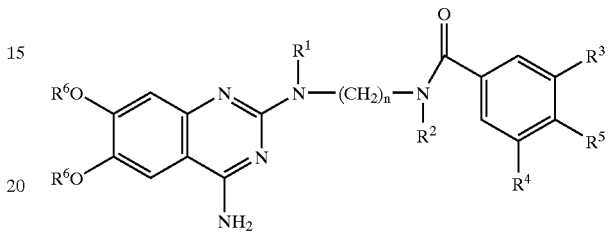

in which $R^1$ and $R^2$ are combined to form an ethylene group;

each of $R^3$ and $R^4$ are t-butyl groups;

$R^5$ represents a hydroxyl group;

$R^6$ and $R^7$ independently represent a hydrogen atom or an alkyl group having 1 to 6 carbon atoms; and n is 2 or 3.

3. The quinazoline derivative of the formula [I] or its pharmaceutically acceptable salt according to claim 1, wherein both of $R^6$ and $R^7$ are methyl groups.

4. The quinazoline derivative of the formula [I] or its pharmaceutically acceptable salt according to claim 1, wherein n is 2.

5. An antihypertensive agent comprising, as an active ingredient, the quinazoline derivative or its pharmaceutically acceptable salt according to claim 1.

* * * * *